United States Patent [19]

Snarey et al.

[11] Patent Number: 4,562,197

[45] Date of Patent: Dec. 31, 1985

[54] ANIMAL GROWTH PROMOTANT L-PYROGLUTAMYL-PYRIDYLALANYL-L-PROLINAMIDES

[75] Inventors: Michael Snarey, Eastry; Peter J. Swift, Wingham, Nr. Canterbury; Michael J. Witty, Dover, all of England

[73] Assignee: Pfizer Inc., New York, N.Y.

[21] Appl. No.: 670,780

[22] Filed: Nov. 13, 1984

[30] Foreign Application Priority Data

Dec. 7, 1983 [GB] United Kingdom ............... 8332704

[51] Int. Cl.[4] .................. C07D 401/14; A61K 31/44
[52] U.S. Cl. .................................. 514/343; 546/281
[58] Field of Search ............................ 546/281; 426/2; 514/343

[56] References Cited

FOREIGN PATENT DOCUMENTS 0080854  6/1963  European Pat. Off. ............ 546/281
1395590  5/1975  United Kingdom ................ 546/281

OTHER PUBLICATIONS

Chemistry of the Amino Acids–Greenstein and Winitz, p. 782, (1961).
Davis et al., "Influence of Chronic Thymotropin–Releasing Hormone Injections ...," Journal of Animal Science, 42, 1244–50, (1976).
McGuffey et al., "Growth Serum Growth Hormone, Thyroxine ...," Journal of Animal Growth, 44, 422–30, (1977).

Primary Examiner—Henry R. Jiles
Assistant Examiner—Dale A. Bjorkman
Attorney, Agent, or Firm—Charles J. Knuth; Peter C. Richardson; James H. Monroe

[57] ABSTRACT

L-pyroglutamyl-pyridylalanyl-L-prolinamides of the formula:

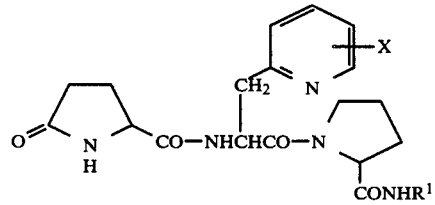

(I)

wherein $R^1$ is H, $C_1$–$C_6$ alkyl, $C_3$–$C_7$ cycloalkyl, $C_2$–$C_8$ alkoxyalkyl or aryl; and X is H, halo, $C_1$–$C_4$ alkyl or $C_1$–$C_4$ alkoxy; and their physiologically acceptable salts and feed compositions thereof are useful for improving the efficiency of feed utilization and/or growth of animals especially poultry.

8 Claims, No Drawings

ANIMAL GROWTH PROMOTANT L-PYROGLUTAMYL-PYRIDYLALANYL-L-PROLINAMIDES

BACKGROUND OF THE INVENTION

This invention relates to the improvement of feed utilisation and growth in economically important animals, and in particular provides compounds which are useful for improving the efficiency of feed utilisation and/or growth of animals, compositions containing such compounds and a method of improving the efficiency of feed utilisation and/or growth of animals by administering the compounds to the animals.

There is a continuing need throughout the world for animal protein for food. One method of improving the efficiency of production of this is by the use of animal feed additives which improve the utilisation of the ingested feed, thereby producing greater weight gain in the animals in the same period of feeding or from the same amount of ingested feed. Other methods include injection, implantation, or incorporation in the drinking water, or substances which have such an effect.

Thyrotropin releasing hormone (TRH) is a naturally occurring tripeptide identified as L-pyroglutamyl-L-histidyl-L-prolinamide which is present in many species of animals. It is a hypothalamic neurohormone which stimulates the release of thyrotropin from the anterior pituitary gland and which is also known to stimulate the release of growth hormone in certain species, which regulates growth of the animal.

TRH has previously been administered by injection into sheep and cattle in an attempt to improve feed utilisation and growth, and it has also been administered to cows to improve milk production. Also recently described, in published European patent application 0080854, is the use of TRH by oral administration to improve feed utilisation and growth in chickens.

We have now discovered that certain analogues of TRH, in particular wherein the histidyl amino-acid residue is replaced by a pyridylalanyl residue, have much improved growth promoting and/or feed utilisation improving properties which make them valuable for administration to economically important food-source animals such as cattle, sheep, pigs and poultry. Also, by virtue of the involvement of TRH in the stimulation of lactation, the compounds are valuable for improving milk production in cows.

SUMMARY OF THE INVENTION

Thus, according to the present invention there are provided L-pyroglutamyl-pyridylalanyl-L-prolinamides of the formula:

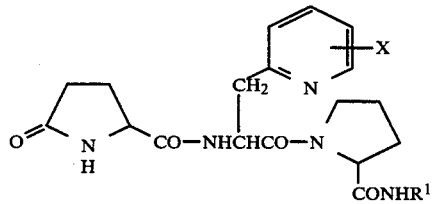

(I)

wherein
$R^1$ is H, $C_1$–$C_6$ alkyl, $C_3$–$C_7$ cycloalkyl, $C_2$–$C_8$ alkoxyalkyl or aryl; and X is H, halo, $C_1$–$C_4$ alkyl or $C_1$–$C_4$ alkoxy;
and their physiologically acceptable salts.

In the compounds of the invention the pyroglutamyl and prolinamide amino-acid residues are both present as the naturally occurring L-isomer. However the pyridylalanyl fragment may be present as the L or D isomer, or as a DL racemic mixture, and the invention includes the separated diastereoisomers as well as mixtures thereof.

In the above definition the term halo includes fluoro, chloro, bromo and iodo. Aryl means phenyl optionally substituted by OH, halo, $C_1$–$C_4$ alkyl or $C_1$–$C_4$ alkoxy groups.

The invention also provides feed compositions for animals comprising a nutritionally balanced feed composition in which is incorporated a growth promoting and/or feed utilisation improving amount of a compound of the formula (I).

The invention also provides compositions, including concentrated feed additives and veterinary compositions, e.g. implants and injectable compositions, containing a compound of the formula (I) together with a suitable diluent or carrier. Also included is a method of improving the efficiency of feed utilisation or growth of economically important animals, or of improving milk production in cows, which comprises administering a compound of the formula (I) or a composition containing a compound of the formula (I) to the animal.

Particularly preferred compounds include those compounds of formula (I) wherein X is H and also wherein $R_1$ is hydrogen.

One particularly preferred compound of the invention is L-pyroglutamyl-DL-2-pyridylalanyl-L-prolinamide.

DETAILED DESCRIPTION OF THE INVENTION

The compounds of the formula (I) are prepared using the standard coupling and protective techniques of amino-acid chemistry. Such procedures are well known to those skilled in the art and are described in standard text books on the subject such as, for example, Greenstein and Winitz "Chemistry of the Amino Acids", published by John Wiley and Sons, New York, 1961.

One synthetic route which we have found to be readily applicable uses a N-protected-pyridylalanine derivative which is first coupled to L-prolinamide and the coupled dipeptide is deprotected and then coupled to L-pyroglutamic acid. The route is shown in the following reaction scheme where P represents a selectively removable nitrogen protecting group and $R^1$ and X are as previously defined.

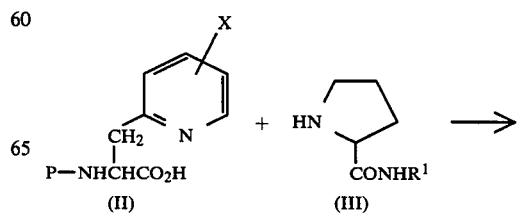

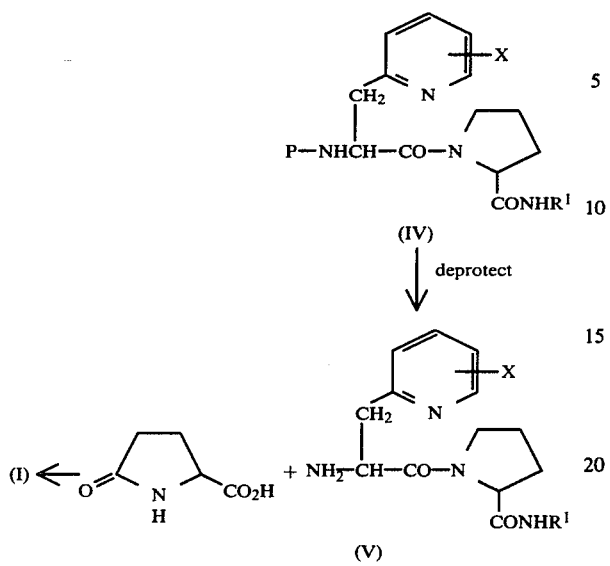

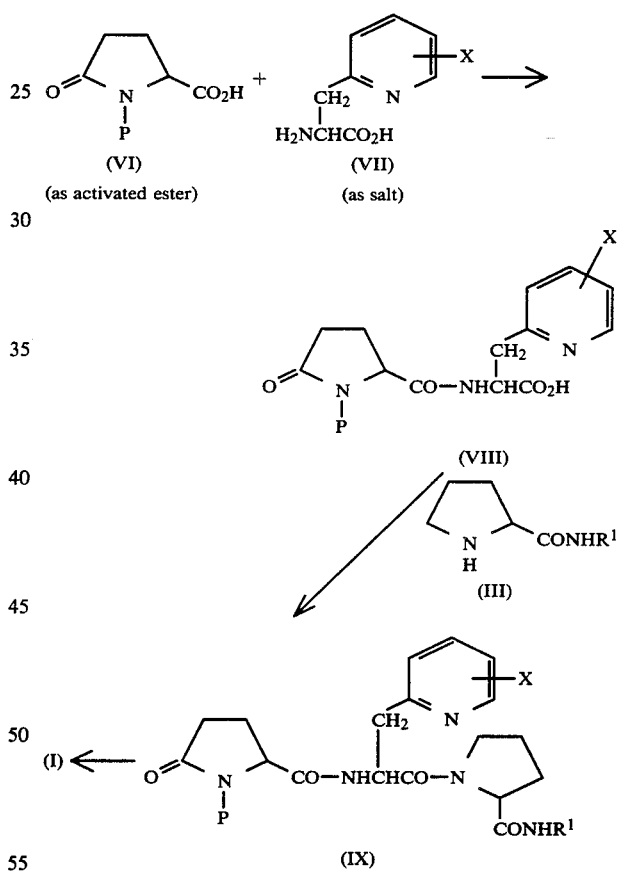

As an initial step in the process, the protected pyridylalanine derivative (II) is coupled to L-prolinamide or an N-substituted derivative thereof (III) wherein $R^1$ is as previously defined. The coupling reaction may be achieved using conventional reagents, for example using N,N-dicyclohexylcarbodiimide, optionally in the presence of 1-hydroxybenzotriazole. Typically the reagents in equimolar amounts are added to an inert organic solvent, e.g. dimethylformamide, and the reaction is allowed to proceed for several hours until the reaction is substantially complete, an overnight period generally being sufficient. The coupled dipeptide (IV) is then isolated using conventional washing and chromatographic techniques and the protecting group P is removed. The conditions employed for deprotection will naturally depend on the particular amino-protecting group employed and the medium employed may be anhydrous or aqueous and in particular instances it will be acidic or basic to various strengths. Examples of protecting groups which we have found to be suitable include the benzyloxycarbonyl group, which is removed by catalytic hydrogenolysis or by treatment with a solution of hydrogen bromide in glacial acetic acid, or the t-butyloxycarbonyl group, which is removed by dissolving the protected dipeptide product in trifluoroacetic acid for several minutes at room temperature. The free dipeptide (V) is finally coupled to L-pyroglutamic acid. The coupling is conveniently achieved by using an activated ester of L-pyroglutamic acid, for example using the 2,4,5-trichlorophenyl ester. The reaction is typically achieved by stirring the reactants in an inert organic solvent e.g. dimethylformamide for an overnight period at room temperature. The product is isolated and purified if required, using conventional techniques, for example by using ion-exchange or gel-filtration chromatography.

In the above sequence, when starting with a racemic D,L-pyridylalanine residue, the product is isolated as a mixture of the two diastereoisomers. However it is also possible to prepare the two individual isomers. This may be done by separating the diastereoisomers of the protected dipeptide (IV) prior to the final coupling step, in which case the separated isomers are deprotected and coupled to the pyroglutamyl fragment as previously described to yield the two tripeptide isomers. Preferably, however, the individual isomers are prepared by separating the diastereoisomers of the final tripeptide products (I). In each case the separation may be achieved, for example, by using column or preparative layer chromatography on silica, or by high pressure liquid chromatography (HPLC) on reverse phase silica. The compound containing the natural L-isomer may be identified by its greater susceptibility to enzymatic digestion, whereas that containing the D-isomers is more resistant to such digestion.

In an alternative process L-pyroglutamic acid, preferably as an N-protected derivative, is first coupled to the pyridylalanine fragment and the resulting dipeptide is then coupled to the L-prolinamide residue (III). Finally the protecting group, if present, is removed. The route is shown in the following reaction scheme in which P represents a selectively removable nitrogen protecting group and $R^1$ and X are as previously defined:

In the first step the optionally N-protected L-pyroglutamic acid (VI) is converted to an activated ester, e.g. the N-hydroxysuccinimide ester, and coupled to the pyridylalanine residue (VII). A salt of pyridylalanine can conveniently be used, for example the sodium salt, and this serves as a blocking group for the carboxylic acid function and avoids the need for a separate protection and deprotection step. As an alternative an ester of pyridylalanine can be employed but in this case the coupled product would need to be hydrolysed to give the dipeptide (VIII). Convenient nitrogen protecting groups for L-pyroglutamic acid are the N-benzyloxycarbonyl or t-butyloxycarbonyl groups. As well as preventing unwanted reactions involving the pyroglutamyl nitrogen atom, the presence of these groups improves solubility in organic solvents which assists subsequent isolation and purification procedures. The coupled dipeptide (VIII) is reacted with the L-prolinamide residue (III), for example using a condensing reagent such as N,N-dicyclohexylcarbodiimide as previously described. Finally the tripeptide (IX) is deprotected to give the compound of formula (I). In the case where the protecting group P is benzyloxycarbonyl this is readily achieved by a conventional hydrogenolysis in the presence of palladium on charcoal catalyst.

In a further variation of this alternative route, the optionally protected L-pyroglutamyl-pyridylalanine dipeptide (VIII) is coupled to L-proline benzyl ester. The benzyl protecting group is then removed by hydrogenation (together with the nitrogen protecting group P, if present) and the tripeptide product is reacted with the amine $R^1NH_2$ using, for example, dicyclohexylcarbodiimide as coupling reagent, to yield the desired amides of formula (I).

The starting materials required for the processes described above are generally known compounds. In particular L-pyroglutamic acid and its N-protected derivatives and L-prolinamide are well known. N-substituted L-prolinamides are readily prepared from L-proline esters by reacting with the appropriate amine $NHR^1$ using standard procedures. 2-Pyridylalanine is a known compound. Pyridylalanine derivatives of formula (VII) wherein X is other than hydrogen are prepared in an analogous manner starting with the appropriate substituted halomethyl-pyridine. The N-protected derivatives (II) are readily prepared by standard procedures as described in the literature.

The growth promoting effect of the compounds of formula (I) is assessed initially by parenteral administration to mice. Weight gain is monitored over a 13 day period and the performance of the mice is compared to that of untreated controls.

In addition the growth promoting properties and improvement in feed utilisation is demonstrated by administration to chickens. The compounds are added to the feed which is provided to the chicks on a free-access basis from shortly after hatching until completion of the trial. At three and four weeks of age the birds are weighed and the live weight gain compared with an untreated control group to give a percentage improvement in live weight gain. The amount of feed consumed is divided by the live weight of the animals in the group at the completion of the trial to give a feed conversion ratio (which gives a measure of the amount of feed required to produce 1 kg increase in body weight), and this is also compared with the control group and the improvement in the feed conversion ratio calculated as a percentage.

The compounds of the invention can be administered either orally or parenterally, but because of their oral activity, they are conveniently administered by adding to the feed supplied to the animals. The compound may be added to a supplementary feed, or to all or only part of the daily feed ration. In practice, addition to the normal mixed feed is preferred because of its greater convenience.

Because only very low levels of the compounds of the invention are needed, care must be taken to ensure even distribution throughout the feed and this is achieved, for example, by adsorbing a solution of the compound onto an inert carrier material, such as cellulose powder, which is then dried and the resulting powder mixed with the feed.

Conventional animal feeds may be used containing, for example, cereals such as maize, corn, wheat or barley; protein sources such as fish or meat by-products; fats; vitamins and minerals; each in an amount sufficient to meet the nutritional requirements of the animals in accordance with standard veterinary practice.

One particular application in which the compounds of the invention have been found to be especially beneficial is in improving the efficiency of feed utilisation and/or promoting growth in poultry, especially chickens. In this instance the compounds of the invention are added to the feed to give a feed utilisation improving and/or growth promotant amount of between 5 and 50,000 µg per kg of feed, a level between 50 and 5,000 µg per kg being more likely to provide useful, most probably between 100 and 1,000 µg per kg. The feed is normally provided to the poultry on a free-access basis from shortly after hatching, (e.g. as day-old chicks), until, or until shortly before slaughter, thereby providing continuous administration of compound throughout the growth of the animals. Naturally, as the birds grow their food intake increases and the amount of compound taken by any particular animal also rises. Thus, for example in the case of chickens given feed containing 500 µg per kg of compound, the average daily intake of compound varies from an approximate level of 10 µg, in the first few days after hatching, up to an approximate level of 50 µg at four weeks of age.

Because of the low levels of additive needed the compounds of the invention are extremely economical. Moreover, while it is possible to administer the compounds on a continuous basis in the feed as described above, it is also possible to administer the compound intermittently, or at specific periods during the growth of the animals.

The compounds may also be administered parenterally (for example by intravenous or subcutaneous injection or by an implant) or as a slow release device. Such techniques will be more valuable with larger animals such as cattle. The compounds may also be administered separately from the feed, for example as a paste, powder, granules, juice, syrup or concentrate or they may be incorporated into a feeding block or lick or some supplementary feed, or added to the drinking water or some other drink, e.g. milk.

Other agents, for example antibiotics, coccidiostats or other medication, may if desired be included in the feed or composition together with a compound of the formula (I) to give additional performance benefits. All of the above compositions are prepared in accordance with acceptable veterinary practice and contain a sufficient amount of a compound of formula (I) to provide the animal with an effective dose of the compound.

The invention is illustrated by the following Examples.

EXAMPLE 1

(1)

N(α)-Benzyloxycarbonyl-D,L-2-pyridylalanyl-L-prolinamide

N(α)-Benzyloxycarbonyl-D,L-2-pyridylalanine (prepared from D,L-2-pyridylalanine by the method of Aganova, et. al., J. Gen. Chem. USSR, 40, 2488 (1979), 450 mg, 1.5 mmole) was dissolved in N,N-dimethylformamide (30 ml) and the solution cooled to 0° C. L-Prolinamide (227 mg, 1.5 mmole), triethylamine (0.21 ml, 1.5 mmole), 1-hydroxybenzotriazole hydrate (230 mg, 1.5 mmole), and N,N'-dicyclohexylcarbodiimide (340 mg, 1.65 mmole) were added and the solution stirred overnight and allowed to warm to room temperature. The solvent was evaporated and the residue taken up in dichloromethane (50 ml) and washed with saturated sodium bicarbonate solution (6×25 ml). The solvent was evaporated and the crude product further purified by gel filtration chromatography on Sephadex G10 (trademark) eluting with aqueous 5% acetic acid. Appropriate fractions were pooled and evaporated, water and toluene being added to remove traces of acetic acid by azeotropic distillation, to give the title compound as a white solid (450 mg, 73%). m.p. 79°–81° C.

Analysis %: Found: C,61.65; H,6.20; N,13.33. $C_{21}H_{24}N_4O_4.0.75H_2O$ requires: C,61.54; H,6.23; N,13.65%.

(2)

L-Pyroglutamyl-D,L-2-pyridylalanyl-L-prolinamide

N(α)-Benzyloxycarbonyl-D,L-2-pyridylalanyl-L-prolinamide (396 mg, 1 mmole) was dissolved in glacial acetic acid containing 45% (w/v) hydrogen bromide (8 ml) and the solution stirred for one hour. Diethyl ether (30 ml) was then added to precipitate the deprotected dipeptide as a yellow solid. The ether was decanted and the residue was dissolved in N,N-dimethylformamide (4 ml). L-Pyroglutamic acid 2,4,5-trichlorophenyl ester (400 mg, 1.32 mmole) was added and the solution cooled to 0° C. The pH of the solution was adjusted to 9 by the addition of triethylamine and the mixture was stirred overnight and allowed to warm to room temperature. The solvent was evaporated and the product taken up in aqueous 25% acetic acid. The solution was filtered several times through a column (1×5 cm) of Amberlite (trademark) IR45 ion-exchange resin in acetate form to remove bromide ions and then evaporated. The product was purified by gel filtration chromatography on Sephadex (trademark) G10 eluting with aqueous 5% acetic acid. Appropriate fractions were pooled and evaporated, traces of solvents being removed by azeotroping with water and toluene to yield the title tripeptide as a white solid (281 mg, 67%). m.p. 130°–135° C.

Analysis %: Found: C,52.31; H,6.16; N,16.19. $C_{18}H_{23}N_5O_4.0.5CH_3CO_2H.1.75H_2O$ requires: C,52.47; H,6.60; N,16.10%.

EXAMPLE 2

Separation of diastereoisomers of product of Example 1

(1) Separation of the diastereoisomers has been achieved by preparative layer chromatography on silica plates using a mixture of chloroform, methanol and 0.880 ammonia (90:10:1) as the developing system. Each of the appropriate bands, identified by uv quenching, was separately removed from the plates and extracted by stirring with methanol for 1 hour. The silica was removed from each by filtration and the solvent evaporated. The residues were each taken up in water and passed down a Sephadex (trade mark) column, eluting with water. The appropriate fractions were pooled, evaporated and freeze dried to give each of the pure separated diastereoisomers as a fine white powder.

Structural assignment was on the basis of enzymic digestion (see J. H. Jones and W. I. Ramage, Int. J. Peptide Protein Res., 14, 65 (1979)).

(2) An alternative method of separating the diastereoisomers has involved using preparative HPLC on a reverse phase, octadecylsilyl-silica column using a water/methanol (80:20) mixture as the mobile phase. Combination and evaporation of the appropriate fractions gave each pure separated diastereoisomer identical in all respects with material purified by the preparative layer chromatography method (1) above.

(a) L-Pyroglutamyl-L-2-pyridylalanyl-L-prolinamide m.p. 120°–123° C. Rf (silica; chloroform, methanol, acetic acid, 10:2:1) 0.33.

Analysis %: Found: C,53.50, H,5.93, N,17.27, $C_{18}H_{23}N_5O_4.1.75H_2O$ requires: C,53.39, H,6.60, N,17.29.

(b) L-Pyroglutamyl-D-2-pyr. Rf (silica; chloroform, methanol, acetic acid, . 121°–123° C10:2:1) 0.28.

Analysis %: Found: C,54.09, H,6.03, N,17.55, $C_{18}H_{23}N_5O_4.1.5H_2O$ requires: C,53.99, H,6.54, N,17.49.

EXAMPLE 3

(1)

N-Benzyloxycarbonyl-L-pyroglutamyl-N-hydroxysuccinimide ester was prepared accordingly to the method of Yanaihara et. al. J. Med. Chem., 16 373 (1973).

(2)

N-Benzyloxycarbonyl-L-pyroglutamyl-D,L-2-pyridylalanine

A solution of 2-pyridylalanine dihydrochloride hydrate (2.57 g, 0.01 mole) in sodium hydroxide solution 3N, 10 ml) was added dropwise over 10 minutes to a stirred solution of N-(benzyloxycarbonyl-L-pyroglutamyl N-hydroxysuccinimide ester in dimethylformamide (20 ml) maintained at 20°–22° C. The resulting colourless emulsion was stirred at 20° C. for 5 hours. The solvent was removed to afford a solid residue which was dissolved in water (35 ml) and neutralised by adding dilute hydrochloric acid (1N, 10 ml). The solution was evaporated to dryness and the residue was stirred with iso-propanol (100 ml), filtered by suction, and the resulting solid washed with diethyl ether and dried under vacuum to give the product as a white solid (1.9 g) m.p. 214°–5° C., $[\alpha]_D^{20}+6.3°$ (c=1, in dimethylformamide).

Analysis %: Found: C,60.84; H,5.19; N,10.13. $C_{21}H_{21}N_3O_6$ requires: C,61.31; H,5.14; N,10.21%.

(3)

N-Benzyloxycarbonyl-L-pyroglutamyl-D,L-2-pyridylalanyl-L-prolinamide

L-Prolinamide (1.44 g, 0.0126 mole) was added to a stirred suspension of N-benzyloxycarbonyl-L-pyroglutamyl-D,L-2-pyridylalanine (4.54 g, 0.0115 mole) in dimethylformamide (50 ml) at 25° C. To the resulting clear solution was added a solution of N,N'-dicyclohexylcarbodiimide (2.6 g, 0.0126 mole) in dimethylformamide (10 ml) in one portion, and the mixture stirred at 25° C. for 20 hours. The resulting dark coloured solution was filtered and evaporated to afford a residue which was stirred with aqueous sodium bicarbonate solution (5%, 150 ml). The suspension was extracted with chloroform (3×100 ml) and the combined extracts were dried over magnesium sulphate and evaporated to give the crude product (6.8 g) which was not purified further, but used directly in the next stage.

(4) L-pyroglutamyl-D,L-2-pyridylalanyl-L-prolinamide

A solution of N-benzyloxycarbonyl-L-pyroglutamyl-D,L-2-pyridylalanyl-L-prolinamide (6.8 g, 0.0138 mole) in a tetrahydrofuran/water mixture (1:1, 250 ml) containing 10% palladium on charcoal catalyst was hydrogenated at 25° C. and 1 atmosphere hydrogen until t.l.c. indicated that the reaction was complete. The resulting suspension was filtered and the filtrate evaporated to yield a gum which was dissolved in water (100 ml), re-filtered and re-evaporated to afford the crude product as a foam (4.5 g). This wash then purified as in Example 1(2) to yield an identical product.

(5) Separation of diastereoisomers

This has been carried out on the crude product of (4) above by the methods described in Example 2, the products obtained being identical to the products of that Example.

EXAMPLE 4

(1) 6-Methylpyrid-2-ylalanine

To a solution of sodium (23 g, 1.0 mole) in ethanol (500 ml) was added diethylacetamidomalonate (106.5 g, 0.49 mole) at 25° C. To this solution was added 2-chloromethyl-6-methylpyridine hydrochloride (0.49 mole, prepared by the method of Baker et al, J. Chem. Soc. Chem. Comm., 3598 (1958)) as a slurry in absolute ethanol (150 ml). The mixture was stirred for 24 hours and then heated at 75° C. for 20 hours. The solvent was then evaporated and the residue extracted with diethyl ether. This solution was evaporated and the crude product recrystallised from a mixture of petroleum ether and ethyl acetate. Further recrystallisation from methanol/water 1:3 and ethyl acetate/petroleum ether gave 2-(diethylacetamidomalonyl)methyl-6-methylpyridine (40.1 g). This product was heated at 100° C. in 6N hydrochloric acid for 26 hours and then allowed to stand at 25° C. for 3 days before evaporating under vacuum to give the desired product as a white solid (36.5 g, 29.6%). m.p. 228°–231° C. (dec.). (Reference: Hanzlik et. al, J. Med. Chem., 22, 424, 1979).

Analysis %: Found: C,42.6; H,5.25; N,11.27, $C_9H_{12}N_2O_2.2HCl$ requires: C,42.71; H,5.57; N,11.07.

(2) N-Benzyloxycarbonyl-L-pyroglutamyl-D,L-(6-methyl-pyrid-2-yl)alanine

This was prepared by the same method as described in Example 3(2) above but starting with 6-methylpyrid-2-ylalanine dihydrochloride (2.53 g, 0.01 mole) as prepared in (1) above. The title compound was obtained as a highly hygroscopic solid and was used directly in the following preparation without further purification.

(3) N-Benzyloxycarbonyl-L-pyroglutamyl-D,L-(6-methyl-pyrid-2-yl)alanyl-L-prolinamide This was prepared by the same method as described in Example 3(3) above but starting with L-prolinamide (0.64 g, 5.58 mmole) and N-benzyloxycarbonyl-L-pyroglutamyl-D,L-(6-methylpyrid-2-yl)alanine (2.37 g, 5.58 mmole) in N,N-dimethylformamide (20 ml) with N,N'-dicyclohexylcarbodiimide (1.26 g, 6.13 mmole). The crude product was purified as described before to give the title compound (2.62 g) (estimated as 73% pure by HPLC on a reverse phase, octadecylsilyl-silica column using 0.1% (w/v) ammonium acetate aqueous solution/methanol (1:1) as mobile phase).

Rf (silica; chloroform, methanol, acetic acid, 10:2:1) 0.42 and 0.47.

(4) L-Pyroglutamyl-D,L-(6-methylpyrid-2-yl)alanyl-L-prolinamide

This was prepared by the method described in Example 3(4) above by hydrogenolysis of N-benzyloxycarbonyl-L-pyroglutamyl-D,L-(6-methylpyrid-2-yl)alanyl-L-prolinamide (2.6 g) in a tetrahydrofuran/water mixture (1:1, 100 ml) containing 10% palladium on charcoal catalyst (50 mg). The same purification procedure gave the title compound as a white amorphous solid (1.35 g).

(5) Separation of diastereoisomers

This has been carried out on the crude product of (4) above by the method described in Example 2(2) to give the two diastereoisomers as white amorphous solids.

Rf (silica; chloroform, methanol, acetic acid, 10:2:1) 0.23.

EXAMPLE 5

(1) 2-Methyl-4-methoxypyridine-N-oxide

To a solution of sodium (4.6 g, 0.2 mole) in anhydrous methanol (140 ml) at 25° C. was added 4-nitro-2-picoline-N-oxide (31 g, 0.2 mole). The mixture was stirred for 1½ hours and then filtered. The filtrate was evaporated and the residue extracted with ethyl acetate. The solution was filtered, evaporated and the oily residue distilled to give the title compound (25.7 g, 92%) b.p. 150° C. at 0.2 mm mercury.

(2) 2-Acetoxymethyl-4-methoxypyridine

To 2-methyl-4-methoxypyridine-N-oxide (23 g, 0.165 mole) in a 1 liter wide necked flask fitted with a large condenser was added ice-cool acetic anhydride (35 ml, 0.37 mole) with stirring. The mixture was allowed to warm to room temperature whereupon a vigorous exothermic reaction occurred. The dark mixture was stirred for 1 hour before evaporating the excess acetic anhydride and distilling the residue to give the title compound (23.26 g, 78%), b.p. 125° C. at 0.1 mm mercury.

(3) 2-Hydroxymethyl-4-methoxypyridine

A solution of 2-acetoxymethyl-4-methoxypyridine (20.72 g, 0.114 mole) in 3M hydrochloric acid (100 ml) was heated under reflux for 1 hour. The resulting solution was concentrated under reduced pressure and the residue neutralised by addition of potassium carbonate. The mixture was extracted with dichloromethane and the organic solution dried over anhydrous sodium sulphate, filtered and evaporated to give a light coloured viscous oil which solidified on standing to yield the title compound (10.6 g, 67%) b.p. 135° C. at 0.1 mm mercury.

(4) 2-Chloromethyl-4-methoxypyridine hydrochloride

This was prepared by the method of Baker et. al., J. Chem. Soc., Chem. Comm., 3598, 1958, but starting with 2-hydroxymethyl-4-methoxypyridine (as prepared in (3) above, 44.05 g, 0.317 mole) and thionyl chloride (500 ml) to give the title compound as a reddish solid, 46 g (75%) which was used directly in the following preparation without further purification.

(5)
2-(Diethylacetamidomalonyl)methyl-4-methoxypyridine

Sodium hydride (23 g of a 60% dispersion in oil, 0.53 mole) was washed free of oil with dry hexane under nitrogen and the solid suspended in dry N,N-dimethylformamide (150 ml). After cooling to 0° C. a solution of diethyl acetamidomalonate (54 g, 0.25 mole) in dry N,N-dimethylformamide (125 ml) was added dropwise over 45 minutes. The suspension was then allowed to warm to room temperature and stirred for 1 hour. 2-Chloromethyl-4-methoxypyridine hydrochloride (45 g, 0.23 mole) was then added portionwise. An exothermic reaction took place and the mixture was stirred for 1 hour. A further aliquot of sodium hydride (5 g of a 60% dispersion, 0.125 mole) was added to force the reaction to completion and the mixture stirred at 15° C. for 16 hours. The solvent was removed under vacuum and the residue triturated with water (350 ml). The pH was adjusted to 7 by addition of 2N hydrochloric acid and the precipitate collected by filtration. The crude product was recrystallised from a mixture of ethyl acetate and hexane to give the title compound (20.3 g, 26%).

Rf (silica; toluene, ethyl acetate,1:1) 0.15.

(6) D,L-(4-Methoxypyrid-2-yl)alanine dihydrochloride 2-(Diethylacetamidomalonyl)methyl-4-methoxypyridine (10.0 g, 29.6 mmole) was stirred and heated under reflux with 2N hydrochloric acid (250 ml) for 4 hours. The solvent was then removed under vacuum and traces of water were removed by azeotropic distillation with ethanol to give the title compound (7.8 g, 98%) which was used directly in the next stage.

Rf (silica, 1M ammonium acetate, ethanol,1:4) 0.25.

(7) L-Pyroglutamyl-D,L(4-methoxypyrid-2-yl)alanine

A solution of (4-methoxypyrid-2-yl)alanine dihydrochloride (0.269 g, 1 mmole) in 3N hydrochloric acid (1.0 ml) was added to a solution of L-pyroglutamic acid-2,4,5-trichlorophenyl ester in N,N-dimethylformamide (3 ml). The mixture was stirred for 1½ hours before pouring into water (5 ml) and extracting with dichloromethane. The aqueous solution was adjusted to pH 3.5 and re-extracted with dichloromethane. Evaporation of the aqueous layer under vacuum gave a gum which was dissolved in methanol and filtered from a small amount of precipitate. Evaporation gave a white amorphous solid which was used in the next stage without further purification.

Rf (silica, 1M ammonium acetate, ethanol,1:4) 0.4.

(8) Preparation and separation of the diastereoisomers of
L-Pyroglutamyl-D,L(4-methoxypyrid-2-yl)alanyl-L-prolinamide L-Pyroglutamyl-D,L-(4-methoxypyrid-2-yl)alanine (3.07 g, 10 mmole) was dissolved in dry N,N-dimethylformamide (20 ml) and L-prolinamide (1.25 g, 11 mmole) was added. To this mixture was added with stirring N,N'-dicyclohexylcarbodiimide (2.26 g, 11 mmole) in dry N,N-dimethylformamide (10 ml). After 24 hours the solution was filtered to remove the precipitated solid and the solvent removed under vacuum. The residue was dissolved in water and extracted with chloroform. The organic solution was dried over sodium sulphate and evaporated to give a gum. This was further purified by column chromatography on silica eluting with 1% methanol in chloroform (by volume) slowly increasing to 10% methanol in chloroform. The appropriate fractions were combined and evaporated to give pure samples of each diastereoisomer of the title compound. L,L,L-isomer yield 650 mg (16%) m.p. 205° C.

Rf (silica; chloroform, methanol, 0.880 ammonia,80:20:1) 0.45.

EXAMPLE 6

(1)
N-Benzyloxycarbonyl-L-pyroglutamyl-D,L-2-pyridylalanyl-L-prolinemethylamide

This was prepared by the method described in Example 3(3) but starting with N-benzyloxycarbonyl-L-pyroglutamyl-D,L-2-pyridylalanine (2.0 g, 5 mmole), L-prolinemethylamide (0.64 g, 5 mmole) and N,N'-dicyclohexylcarbodiimide (1.03 g, 5 mmole) in dry N,N-dimethylformamide (20 ml). After 72 hours the reaction was worked up as previously described to give a crude product which was used directly in the next stage without further purification. Yield 2.7 g.

Rf (silica; chloroform, methanol, acetic acid, 10:2:1) 0.6.

(2)
L-Pyroglutamyl-D,L-2-pyridylalanyl-L-prolinemethylamide

This was prepared by the method described in Example 3(4) using crude N-benzyloxycarbonyl-L-pyroglutamyl-D,L-2-pyridylalanyl-L-prolinemethylamide (1.25 g) from (1) above in a tetrahydrofuran/water 1:1 mixture (50 ml). When reaction was complete, filtration and evaporation under vacuum gave a brown oil (900 mg).

Rf (silica; chloroform, methanol, acetic acid, 10:2:1) 0.22 and 0.25.

(3) Separation of diastereoisomers

This was accomplished by the method described in Example 2(2) except that a mixture of 0.1% v/v acetic acid in water/methanol 87:13 was used as the mobile phase. Appropriate fractions eluting from the column were combined to give a pure sample of L-pyroglutamyl-L-2-pyridylalanyl-L-prolinemethylamide as a white amorphous solid.

EXAMPLE 7

L-Pyroglutamyl-D,L-2-pyridylalanyl-L-proline ethylamide

This compound was prepared by the method described in Example 6 but starting with proline ethylamide (0.8 g, 5.6 mmole) instead of proline methylamide. Hydrogenolysis of the resulting N-benzyloxycarbonyl-L-pyroglutamyl-D,L-2-pyridylalanyl-L-proline ethylamide gave the product as a reddish brown solid. Purification and separation of the two diastereoisomers was achieved by preparative HPLC as previously described.

Rf (silica; chloroform,methanol,acetic acid, 10:2:1) 0.4.

EXAMPLE 8

L-Pyroglutamyl-D,L-2-pyridylalanyl-L-proline phenylamide

This compound was prepared by the method described in Example 6 but starting with proline phenylamide (1.05 g, 5.5 mmole) instead of proline methylamide. Hydrogenolysis of the resulting N-benzyloxycarbonyl-L-pyroglutamyl-D,L-2-pyridylalanyl-L-proline phenylamide gave the title product as a solid (1.68 g).

Purification and separation of the two diastereoisomers was achieved by column chromatography on silica (200 g) eluting with chloroform/methanol 9:1 to give L-pyroglutamyl-L-2-pyridylalanyl-L-proline phenylamide, m.p. 95°–98° C.

Rf (silica; chloroform, methanol,9:1) 0.35.

EXAMPLE 9

(1) L-Pyroglutamyl-D,L-2-pyridylalanine

To a suspension of L-pyroglutamic acid-2,4,5-trichlorophenyl ester (7.75 g, 25 mmole) in dry N,N-dimethylformamide (20 ml) was added a solution of 2-pyridylalanine dihydrochloride hydrate (2.57 g, 10 mmole) in 3N sodium hydroxide solution (10 ml) at 25° C. The temperature of the mixture rose to 42° C. and the solution was stirred for 1½ hours before pouring into water (100 ml). The pH was adjusted to 3.5 by addition of 2M HCl and the solution was extracted with chloroform (100 ml). The aqueous layer was separated and evaporated to give a gum which was triturated with methanol (50 ml). The supernatant was filtered and evaporated to give a white solid which was dried by azeotropic distillation with N,N-dimethylformamide. This material was pure enough to use directly in the following preparation.

Rf (silica; ethanol, 1M ammonium acetate,4:1) 0.3.

(2) L-Pyroglutamyl-D,L-2-pyridylalanyl-L-proline benzyl ester

To a stirred suspension of L-pyroglutamyl-D,L-2-pyridylalanine (10 mmole) in dry N,N-dimethylformamide (20 ml) was added L-proline benzyl ester hydrochloride (2.3 g, 10 mmole) followed by N-methylmorpholine (1.1 g, 11 mmole) at room temperature. After 5 minutes a solution of N,N'-dicyclohexycarbodiimide (2.2 g, 11 mmole) in dry N,N-dimethylformamide (80 ml) was added. After 72 hours the suspension was filtered and the solution evaporated under vacuum to give an oil. This was added to water (60 ml) and the suspension was extracted with dichloromethane (3×70 ml). The combined extracts were washed with sodium hydrogen carbonate solution, dried over magnesium sulphate and evaporated under vacuum to give the title compound (4.2 g). Further purified by column chromatography on silica, eluting with chloroform/methanol (9:1) gave the product as an amorphous solid (3.6 g, 78%) which was used directly in the next stage.

Rf (silica; chloroform, methanol,9:1) 0.35 and 0.40.

(3) L-Pyroglutamyl-D,L-2-pyridylalanyl-L-proline

L-pyroglutamyl-D,L-2-pyridylalanyl-L-proline benzyl ester (1.0 g) was dissolved in a mixture of tetrahydrofuran (30 ml) and water (20 ml) and 10% palladium on charcoal (100 mg) was added. The mixture was stirred under hydrogen at atmospheric pressure until no starting material remained. Filtration and evaporation under vacuum gave the title compound (710 mg) which was sufficiently pure to use in the following preparation.

Rf (silica; ethanol, 1M ammonium acetate,4:1) 0.37 and 0.45.

(4) Preparation and separation of the diastereoisomers of L-Pyroglutamyl-D,L-2-pyridylalanyl-L-proline 2-methoxyethylamide To a solution of L-pyroglutamyl-D,L-2-pyridylalanyl-L-proline (3.0 g, 8 mmole) and 1-hydroxybenzotriazole hydrate (2.16 g, 16 mmole) in dry dichloromethane (50 ml) at 0° C. was added N,N-dicyclohexylcarbodiimide (1.81 g, 8.8 mmole) in dry dichloromethane (50 ml). After 5 minutes a solution of 2-methoxyethylamine (0.66 g, 8.8 mmole) in dry dichloromethane (10 ml) was added dropwise and the mixture was stirred at 25° C. for 3 hours. The precipitated solid was removed by filtration and the solution evaporated. The residue was dissolved in chloroform, washed with sodium hydrogen carbonate solution, dried over sodium sulphate and evaporated under vacuum to give the crude product. Partial purification and isomer separation was achieved by column chromatography on silica. The appropriate fractions containing the individual diastereoisomers were combined and evaporated and each was further purified by ion exchange chromatography (Bio-Rad AG 50WL-X8 (trade name) cation exchange resin) eluting the product with 2% v/v pyridine in water. Evaporation of the appropriate fractions gave the two diastereoisomers of the title compound as highly hygroscopic white amorphous solids.

Rf (silica; chloroform, methanol, ammonia, 80:20:1) 0.40 and 0.45.

The final products of Examples 1 to 9 have each been assessed for growth promoting activity in mice by subcutaneous administration at dose levels from 1 to 10 mg/kg per day. All have been found to be effective at levels within this range.

EXAMPLE 10

Poultry feed compositions for broiler chickens were prepared of the following composition.

| Ingredients | % |
| --- | --- |
| Maize | 49.0 |
| Wheat | 12.0 |
| Herring | 4.0 |
| Meat and Bone Meal | 8.0 |
| Soya | 25.0 |
| Liquid Fat | 1.5 |
| Methionine | 0.16 |
| Salt | 0.25 |
| Vitamin Premix | 0.2 |

The compound of Example 1(55 mg) was dissolved in methanol (300 ml) and this was added to a slurry of Avicel (trademark, 100 g) in methanol (1200 ml). This mixture was stirred for 1 hour and the methanol was then removed using a rotary evaporator. The resulting powder was thoroughly mixed with 25 kg of the above feed to give a premix which was finally mixed with a further 85 kg of the same feed to give 110 kg of product containing 500 µg of the compound of Example 1 per kg of feed.

| Typical Analyis (as fed basis) | |
| --- | --- |
| Oil (%) | 5.21 |

| Typical Analyis (as fed basis) | |
|---|---|
| Protein (%) | 22.65 |
| Fibre (%) | 3.5 |
| Energy content (MJ/kg) | 12.71 |

Feed compositions were similarly prepared containing the compound of Example 1 in amounts of 150, 450, 900 and 2000 µg/kg of mixed feed, and compositions are similarly prepared containing the compounds of Examples 2 to 9.

EXAMPLE 11

The growth promoting and feed efficiency improving properties of the compounds of the Examples in poultry are shown by the following feeding trial using one-day old broiler chicks.

The chickens are housed in two ventilated and temperature controlled rooms, each divided into two blocks of sixteen floor-pens. Day old, sexed, broiler strain chicks are allocated by sex, fifteen to each of the designated male or female pens. Treatments and controls are randomly allocated to the pens such that eight pens are used for each treatment regime, each treatment being represented twice in each block.

The feed compositions containing various amounts of the compounds of the invention, prepared as described in Example 10, are provided to the chicks on a free access basis. Records are kept of mortality and of the amount of feed supplied to each pen. At three and four weeks of age all birds are weighed and the weight of all uneaten feed recorded. The live weight gain of the birds is calculated and compared with an untreated control group to give a percentage difference in live weight. Similarly the amount of feed consumed is divided by the live weight of the animals in the group to give a feed conversion ratio (which gives a measure of the amount of feed required to produce 1 kg increase in body weight), and this is also compared with the control group and the % difference calculated.

Results obtained in such trials have indicated that the compound of Example 1, when added to the feed at levels of from 150 to 2000 µg/kg, is effective in increasing the growth of the chickens and in improving feed conversion efficiency.

We claim:

1. A L-Pyroglutamyl-pyridylalanyl-L-prolinamide of the formula:

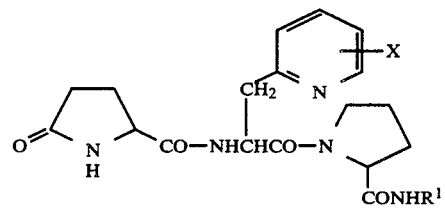

or a pharmaceutically acceptable salt thereof, wherein:
$R^1$ is hydrogen, $C_1$–$C_6$ alkyl, $C_3$–$C_7$ cycloalkyl, $C_2$–$C_8$ alkoxyalkyl or phenyl optionally substituted by OH, halo, $C_1$–$C_4$ alkyl, or $C_1$–$C_4$ alkoxy groups; and
X is hydrogen halo, $C_1$–$C_4$ alkyl or $C_1$–$C_4$ alkoxy.

2. A compound according to claim 1 wherein X is hydrogen.

3. A compound according to claim 2 wherein $R^1$ is hydrogen.

4. A compound according to claim 1 wherein $R^1$ is hydrogen.

5. A compound according to claim 1 which is L-Pyroglutamyl-DL-2-pyridylalanyl-L-prolinamide.

6. A feed composition for economically important food-source animals comprising a nutritionally balanced feed composition incorporating a growth promoting or feed utilization improving amount of a compound according to claim 1.

7. A composition for improving the efficiency of feed utilization or growth of economically important food-source animals comprising a compound according to claim 1 and a suitable diluent or carrier.

8. A method of improving the efficiency of feed utilization or growth of economically important animals food-source animals which comprises administering a growth promoting or feed utilization improving amount of a compound according to claim 1 to the animal.

* * * * *